United States Patent
Sakaguchi et al.

(10) Patent No.: US 7,892,843 B2
(45) Date of Patent: Feb. 22, 2011

(54) NICKEL CRUCIBLE FOR MELTING ANALYTICAL SAMPLE, METHOD OF PREPARING ANALYTICAL SAMPLE AND METHOD OF ANALYSIS

(75) Inventors: Masahiro Sakaguchi, Ibaraki (JP); Mitsuru Yamaguchi, Ibaraki (JP); Tomio Takahashi, Ibaraki (JP); Kouichi Takemoto, Ibaraki (JP)

(73) Assignee: JX Nippon Mining & Metals Corporation, Tokyo (JP)

( * ) Notice: Subject to any disclaimer, the term of this patent is extended or adjusted under 35 U.S.C. 154(b) by 309 days.

(21) Appl. No.: 12/278,889

(22) PCT Filed: Feb. 15, 2007

(86) PCT No.: PCT/JP2007/052711

§ 371 (c)(1),
(2), (4) Date: Aug. 8, 2008

(87) PCT Pub. No.: WO2007/097241

PCT Pub. Date: Aug. 30, 2007

(65) Prior Publication Data

US 2010/0167407 A1  Jul. 1, 2010

(30) Foreign Application Priority Data

Feb. 22, 2006  (JP) ............................. 2006-044717

(51) Int. Cl.
G01N 33/20 (2006.01)
B01N 3/00 (2006.01)
G01N 1/22 (2006.01)

(52) U.S. Cl. .......................... 436/84; 436/75; 436/181; 422/102

(58) Field of Classification Search .................... 436/84, 436/75, 181; 422/102
See application file for complete search history.

(56) References Cited

U.S. PATENT DOCUMENTS

| 3,000,703 A | 9/1961 | Brugger |
| 3,758,662 A | 9/1973 | Tobin et al. |
| 4,946,490 A | 8/1990 | Hall et al. |

(Continued)

FOREIGN PATENT DOCUMENTS

| JP | 45-038971 A | 12/1970 |
| JP | 10-132801 A | 5/1998 |
| JP | 2004-069413 A | 3/2004 |
| JP | 2004-069413 | * 4/2004 |

OTHER PUBLICATIONS esp@cenet database, One Page English Abstract of JP 10-038773 A, Feb. 13, 1998.
esp@cenet database, One Page English Abstract of JP 02-172540 A, Jul. 4, 1990.

(Continued)

*Primary Examiner*—Robert J Hill, Jr.
*Assistant Examiner*—Dwan A Gerido
(74) *Attorney, Agent, or Firm*—Howson & Howson LLP

(57) ABSTRACT

A nickel crucible used for melting an analytical sample in the pretreatment of the analytical sample, characterized in that the purity of the nickel crucible is 99.9999 wt % or higher. Also provided is a method of analysis, comprising melting a sample by the use of the nickel crucible for melting having a purity of 99.9999 wt % or higher, and analyzing the melt to thereby obtain an analytical result in which the respective lower limits of determination of Mn, Al, Si, Mg, Pb, Fe, Co, Ti, Cu, Cr, Zr, Mo, and W are Mn: 5 wtppm, Al: 10 wtppm, Si: 10 wtppm, Mg: 5 wtppm, Pb: 5 wtppm, Fe: 5 wtppm, Co: 5 wtppm, Ti: 20 wtppm, Cu: 20 wtppm, Cr: 10 wtppm, Zr: 5 wtppm, Mo: 2 wtppm, and W: 10 wtppm. In light of the recent analytical technology demanded of fast and accurate measurement of high purity materials, high purity analysis is attained through inhibition of mixing of impurities from the crucible.

5 Claims, 3 Drawing Sheets

Measuring Impurities of Zr, Si, Fe, Al in $SnO_2$

U.S. PATENT DOCUMENTS

| | | | |
|---|---|---|---|
| 5,336,378 A * | 8/1994 | Nishimura et al. | 205/400 |
| 6,723,672 B1 | 4/2004 | Stuart et al. | |
| 2004/0002762 A1 | 1/2004 | Hawkins | |
| 2005/0221088 A1 | 10/2005 | Celik et al. | |
| 2007/0051440 A1 | 3/2007 | Eucken | |
| 2009/0053112 A1 | 2/2009 | Shindo et al. | |
| 2009/0104082 A1 | 4/2009 | Sakaguchi et al. | |

OTHER PUBLICATIONS esp@cenet database, One Page English Abstract of JP 58-048854 A, Mar. 22, 1983.

U.S. Office Action dated Oct. 1, 2010 issued in co-pending U.S. Appl. No. 12/297,789.

U.S. Office Action dated Aug. 17, 2010 issued in co-pending U.S. Appl. No. 12/188,446.

* cited by examiner

Measuring Impurities of Zr, Si, Fe, Al in $SnO_2$

NICKEL CRUCIBLE FOR MELTING ANALYTICAL SAMPLE, METHOD OF PREPARING ANALYTICAL SAMPLE AND METHOD OF ANALYSIS

BACKGROUND OF THE INVENTION

The present invention relates to a nickel crucible for melting an analytical sample, a preparation method of such analytical sample, and a method of analysis that enables high precision analysis by inhibiting the mixture of impurities from the crucible regardless of who or how skilled the analyst is.

In recent years, demands for measuring high purity materials quickly and accurately are on the rise. Particularly, since persistent samples are increasing in recent years, a flux with stronger oxidizing power is in demand.

A persistent sample is generally prepared by melting the sample with a flux. The process of melting the sample with a flux is usually based on a melting method such as carbonate (alkali) fusion, alkali hydroxide fusion, sodium peroxide fusion, or sodium hydrogensulfate fusion. Nevertheless, if a flux with strong oxidizing power is used, the crucible itself will wear easily, and, consequently, there is a problem in that impurities will be eluted in the crucible.

In other words, according to the increase of the foregoing demands, there is a problem in that the measured values differs due to the influence of contamination from the used equipment, and often reanalysis must be performed in order to confirm the reliability of the initial analysis.

As described above, since a conventional nickel crucible for melting a sample has a purity level of 99wt % (2N), there is a problem in that the lower limit of determination will increase due to the mixture of impurities from the crucible, and such conventional nickel crucible cannot be used for analyzing the recent high purity samples. Nevertheless, conventionally, no attention was particularly given to the purity of crucibles, and the situation ends with that the measurements were merely conducted several times or the pretreatment process was devised in certain ways.

Although there are not many Patent Documents that describe an analytical means to handle the foregoing high purity materials, take some materials that may be of reference, for instance, there is technology that relates to the method of adjusting a sample for performing qualitative and quantitative analysis of such sample, whereby the sample is placed on a metal foil and subject to thermolysis together with such metal foil, and further made into a solution (Patent Document 1). Nevertheless, this is an extremely atypical type of method, and lacks versatility.

Further, a chemical analysis crucible composed from Pt alloy or Pd alloy in which 5 to 90wt % of Pd is added to Pt that uses an alkali flux to perform chemical analysis of ores is disclosed (Patent Document 2). Nevertheless, this technology is subject to the use of expensive crucible materials, and there is a problem in that it is impractical since an alloy will be formed depending on the sample elements.

In addition, a method of analyzing the rhodium content in a film by heating and melting a rhodium-ruthenium alloy plating film in a nickel crucible with sodium peroxide or potassium peroxide is disclosed (Patent Document 3). Nevertheless, Patent Document 3 does not in any way disclose the purity of the crucible. Thus, it is strongly assumed that the crucible of Patent Document 3 has a conventional purity level (2N level). Thus, there is a problem in that the lower limit of determination is high due to the inclusion of impurities, and high precision analysis cannot be performed.

[Non-Patent Document 1] "Analysis" Introductory Course, Issued in October 1979, "Reagent Used in Dissolution" Pages 648 to 655

[Patent Document 1] Japanese Patent Laid-Open Publication No. H10-38773

[Patent Document 2] Japanese Patent Laid-Open Publication No. H2-172540

[Patent Document 3] Japanese Patent Laid-Open Publication No. S58-48854

SUMMARY OF THE INVENTION

In light of the recent analytical technology demanded of fast and accurate measurement of high purity materials, an object of the present invention is to provide a nickel crucible for melting an analytical sample, a preparation method of such analytical sample, and a method of analysis that enables high precision analysis by inhibiting the mixing of impurities from the crucible regardless of who or how skilled the analyst is.

In order to achieve the foregoing object, the present invention provides:

1) A nickel crucible used for melting an analytical sample in the pretreatment of the analytical sample, wherein the purity of the nickel crucible is 99.9999 wt % or higher;
2) The nickel crucible used for melting according to paragraph 1) above which uses a basic flux comprising one or more types of alkali chemicals selected from $Na_2CO_3$, $K_2CO_3$, $H_3BO_3$, NaOH, KOH, $Na_2B_2O_7$, $Li_2B_2O_7$ and the like, or a basic flux added with one or more types of oxidizing agents selected from $Na_2O$, $Na_2O_2$, $K_2O$, $K_2O_2$, $KNO_3$, $KClO_3$ and the like, or one or more types of acid flux selected from $Na_2S_2O_7$, $K_2S_2O_7$, $NaHSO_4$ and the like to melt the analytical sample. A list of basic flux is on Table 1 below;
3) A method of preparing an analytical sample using a high purity nickel crucible, including a step of preliminarily melting a sample in a nickel crucible having a purity of 99.9999 wt % or higher to obtain the analytical sample;
4) The method of preparing an analytical sample according to paragraph 3) above, further including a step of measuring and placing a sample in the crucible, and melting the sample using a basic flux comprising one or more types of alkali chemicals selected from $Na_2CO_3$, $K_2CO_3$, $H_3BO_3$, NaOH, KOH, $Na_2B_2O_7$, $Li_2B_2O_7$ and the like, or a basic flux added with one or more types of oxidizing agents selected from $Na_2O$, $Na_2O_2$, $K_2O$, $K_2O_2$, $KNO_3$, $KClO_3$ and the like, or one or more types of acid flux selected from $Na_2S_2O_7$, $K_2S_2O_7$, $NaHSO_4$ and the like to obtain the analytical sample; (See Table 1)
5) A method of analysis, comprising of melting a sample using a nickel crucible used for melting having a purity of 99.9999 wt % or higher, and analyzing the result to obtain an analytical result in which the respective lower limits of determination of Mn, Al, Si, Mg, Pb, Fe, Co, Ti, Cu, Cr, Zr, Mo, and W are Mn: 5 wtppm, Al: 10 wtppm, Si: 10 wtppm, Mg: 5 wtppm, Pb: 5 wtppm, Fe: 5 wtppm, Co: 5 wtppm, Ti: 20 wtppm, Cu: 20 wtppm, Cr: 10 wtppm, Zr: 5 wtppm, Mo: 2 wtppm, and W: 10 wtppm.

TABLE 1

| Basic Flux | | |
|---|---|---|
| Alkali | Oxidizing Agents | Acid Flux |
| $Na_2CO_3$, $K_2CO_3$, $H_3BO_3$, NaOH, KOH, $Na_2B_2O_7$, $Li_2B_2O_7$, etc. | $Na_2O$, $Na_2O_2$, $K_2O$, $K_2O_2$, $KNO_3$, $KClO_3$, etc. | $Na_2S_2O_7$, $K_2S_2O_7$, $NaHSO_4$, etc. |

As a result of using the high purity nickel crucible in which the purity of the nickel crucible is 99.9999 wt % or higher, the present invention yields a superior effect in that it is able to inhibit the mixing of impurities from the crucible and perform high purity analysis, save the labor time and mitigate the amount of reagent to be used, and, therefore, the present invention meets the demands of recent analytical technology which requires fast and accurate measurement of high purity materials.

DETAILED DESCRIPTION OF THE INVENTION

As the nickel crucible used for melting an analytical sample in the pretreatment of such analytical sample according to the present invention, a nickel crucible having a purity of 99.9999 wt % or higher is used.

Figure 1:
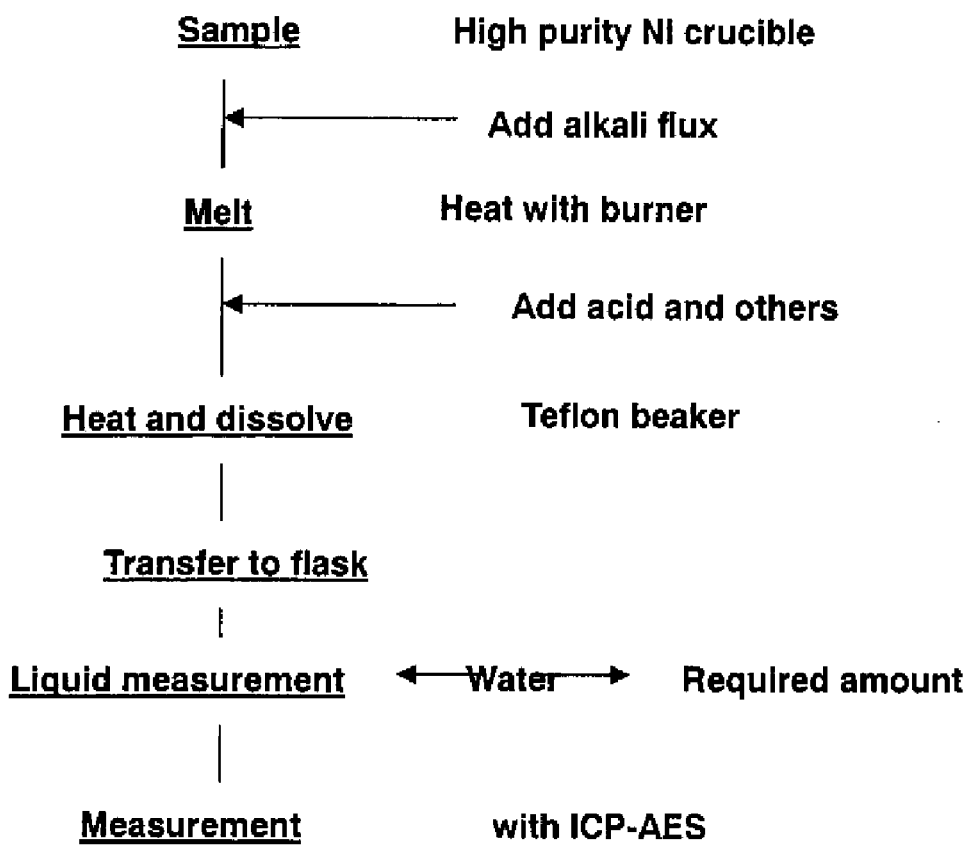
FIG. 1 is a schematic explanatory diagram explaining the analytical process of Example 1.

The general procedures for performing the analysis of the present invention are as follows. The outline of these analytical procedures is shown in FIG. 1.

(1) Place the sample in the nickel crucible.
(2) Add a flux, such as an alkali flux, to the crucible.
(3) Heat the crucible with a burner or a muffle furnace and melt the flux and sample.
(4) Transfer the sample to a PTFE beaker or the like.
(5) Add acid and the like.
(6) Heat the beaker and dissolve the sample.
(7) Transfer the sample to a volumetric flask.
(8) Add water until the liquid measure becomes a prescribed value.
(9) Measure the result with an ICP-AES or the like.

As a result of using the foregoing nickel crucible for melting having a purity of 99.9999 wt % or higher to melt the sample, and thereafter analyzing such sample, the present invention yields a superior effect of obtaining an analytical result where the respective lower limits of determination of Mn, Al, Si, Mg, Pb, Fe, Co, Ti, Cu, Cr, Zr, Mo, and W are Mn: 5 wtppm, Al: 10 wtppm, Si: 10 wtppm, Mg: 5 wtppm, Pb: 5 wtppm, Fe: 5 wtppm, Co: 5 wtppm, Ti: 20 wtppm, Cu: 20 wtppm, Cr: 10 wtppm, Zr: 5 wtppm, Mo: 2 wtppm, and W: 10 wtppm.

EXAMPLES

The present invention is now explained based on the Example and Comparative Example. This Example merely illustrates a preferred example, and the present invention shall in no way be limited thereby. In other words, all modifications, other embodiments and modes covered by the present invention shall be included in this invention.

Example 1

The Example of the present invention used a high purity nickel crucible having a purity of 99.9999 wt %, quantitative determination of impurities such as Zr, Si, Fe, and Al in $SnO_2$ was performed. The analytical procedures are explained with reference to FIG. 1. The analytical conditions and analytical results were as follows.

A sample in the amount of 1 g was placed in the foregoing high purity nickel crucible, and a prescribed amount (several grams) of KOH and $KNO_3$ were respectively added to the sample. The sample was heated with a burner, and subsequently added with 20 ml of hydrochloric acid (HCl) and 50 ml of ultrapure water.

The sample was transferred to a 300 ml teflon beaker, and heated and dissolved. After dissolution, the total volume was placed in a 250 ml flask, ultrapure water was added thereto, and the liquid measure was prescribed. The obtained sample was measured with an ICP-AES.

The measurement result of primary impurities in comparison to a case of using a Ni crucible having a purity of 99% is shown in Table 2.

TABLE 2

Comparison of Analysis Result of Impurities in $SnO_2$

| Crucible Type | High Purity Nickel Crucible of Present Invention | | Conventional Nickel Crucible (2N) | |
|---|---|---|---|---|
| Analysis Element | Average | Standard Variation | Average | Standard Variation |
| Mn | 0.11 | 0.15 | 1700 | 270 |
| Si | 3.0 | 0.82 | 1000 | 160 |
| Mg | 0.32 | 0.11 | 220 | 36 |
| Pb | 0.17 | 0.16 | 220 | 37 |
| Fe | 7.6 | 0.63 | 66 | 9.0 |
| Co | 1.4 | 0.99 | 220 | 34 |
| Ti | 53 | 15 | 230 | 37 |
| Cu | 1.9 | 0.8 | 74 | 12 |
| Cr | 1.5 | 0.4 | 33 | 5.2 |

Unit: wtppm: µg/g

As shown in Table 3, by the use of the high purity nickel crucible of the present invention, the lower limit of determination can be lowered significantly, and a superior effect of conducting the quantitative determination of Zr, Si, Fe, Al and so on with a single operation was obtained.

In other words, in a case of using a nickel crucible having a purity level of 2N, since the purity is low, significant amounts of Al, Si, Fe and so on are eluted from the nickel crucible. Thus, in the foregoing case, a zirconium crucible must be used. Nevertheless, as shown in the Example, a material requiring the quantitative determination of zirconium cannot be measured using a zirconium crucible.

Accordingly, analysis had to be performed several times to lower the lower limit of determination in order to conduct the foregoing analysis, but Example 1 of the present invention enabled to perform quantitative determination with a single operation.

The lower limit of determination was defined as 10 times the standard deviation (s) based on the measurement of 6 blank samples, and the numerical values shown in Table 3 indicate the lower limits.

TABLE 3

Determination Lower Limit of Nickel Crucibles of Conventional and Present Invention

| Analysis Element | Conventional Nickel Crucible Uinit (wtppm: µg/g) | High Purity Nickel Crucible of Present Invention Uinit (wtppm: µg/g) |
|---|---|---|
| Mn | 1000 | 5 |
| Al | 1000 | 10 |
| Si | 500 | 10 |
| Mg | 100 | 5 |
| Pb | 100 | 5 |
| Fe | 500 | 5 |

TABLE 3-continued

Determination Lower Limit of Nickel Crucibles of Conventional and Present Invention

| Analysis Element | Conventional Nickel Crucible Uinit (wtppm: μg/g) | High Purity Nickel Crucible of Present Invention Uinit (wtppm: μg/g) |
|---|---|---|
| Co | 100 | 5 |
| Ti | 100 | 20 |
| Cu | 50 | 20 |
| Cr | 20 | 10 |
| Zr | 10 | 5 |
| Mo | 10 | 2 |
| W | 10 | 10 |

*the determination lower limit was defined as ten times the standard deviation (s) based on the measurement of six blank samples Comparative Example 1

In Comparative Example 1, a commercially available nickel crucible having a purity of 99 wt % was used instead of the high purity Ni crucible among the analytical procedures of FIG. 1, and the quantitative determination of impurities such as Zr, Si, Fe, and Al in $SnO_2$ was performed as with Example 1.

The following working method was the same as Example 1 in both cases of using a nickel crucible and using a zirconium crucible. In other words, a sample in the amount of 1 g was placed in the foregoing nickel crucible and zirconium crucible, and a prescribed amount (several grams) of KOH and $KNO_3$ were respectively added to the sample. The sample was heated with a burner, and subsequently added with 20 ml of hydrochloric acid (HCl) and 50 ml of ultrapure water. Subsequently, the sample was transferred to a 300 ml teflon beaker, and heated and dissolved.

After dissolution, the total volume was placed in a 250 ml flask, ultrapure water was added thereto, and the liquid measure was prescribed. The obtained sample was measured with an ICP-AES.

The measurement result in comparison to Example 1 is shown in Table 2.

Since the conventional nickel crucible had a low purity level of 2N, the impurity content was high, contamination from the crucible was significant when such conventional nickel crucible was used for analyzing the impurities in the sample persistent to acid, and the analytical results showed abnormal figures.

In particular, manganese (Mn), silicon (Si), iron (Fe), and aluminum (Al) attained high values. Thus, although it is necessary to reduce the lower limit of determination of impurities, it is evident that such reduction cannot be realized.

Figure 2:
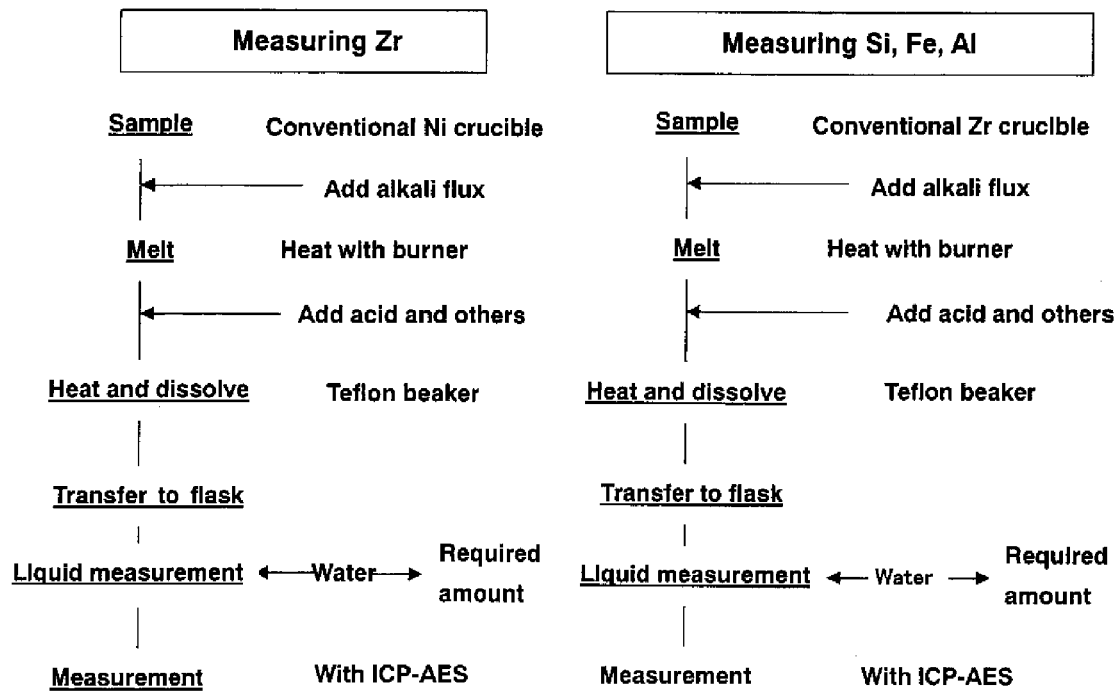
FIG. 2 is a schematic explanatory diagram explaining the analytical process of Comparative Example 1.

In light of the above, as shown in Table 2, significant amounts of Al, Si, Fe and the like are eluted from the nickel crucible with the use of a nickel crucible having a purity level of 2N since the purity is low. Thus, a nickel crucible cannot be used for analyzing Al, Si, Fe and the like, and a zirconium crucible must be used in this case. As a result, it is necessary to analyze Zr and other components according to separate procedures as shown in FIG. 2, and this required twice the labor time in comparison to Example 1.

The lower limit of determination was defined as 10 times the standard deviation (s) based on the measurement of 6 blank samples, and the numerical values shown in Table 3 similarly indicate the lower limits in the Comparative Example. Results of the lower limit of determination of primary impurity elements in the case of using a conventional lower purity nickel crucible of Table 3 and the high purity nickel crucible of the present invention are shown in FIG. 3.

Figure 3:
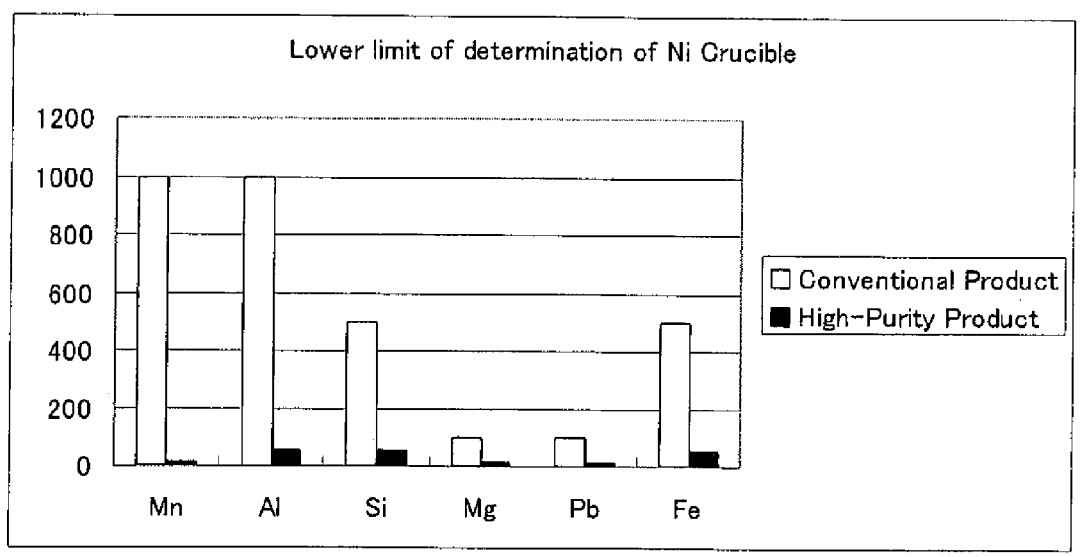
FIG. 3 is a diagram showing the lower limit of determination of the high purity nickel crucible of the present invention and the lower limit of determination of a conventional nickel crucible.

As shown in Table 3 and FIG. 3, there is a significant difference in the lower limit of determination in the Example and the Comparative Example, and it has been confirmed that the lower limit of determination of the present invention showed considerable improvement.

Although the sample was dissolved using KOH and $KNO_3$ in the foregoing Example, the same results were obtained with the use of other fluxes, such as a basic flux comprising one or more types of alkali chemicals selected from $Na_2CO_3$, $K_2CO_3$, $H_3BO_3$, NaOH, KOH, $Na_2B_2O_7$, $Li_2B_2O_7$ and the like, or a basic flux added with one or more types of oxidizing agents selected from $Na_2O$, $Na_2O_2$, $K_2O$, $K_2O_2$, $KNO_3$, $KClO_3$ and the like, or one or more types of acid flux selected from $Na_2S_2O_7$, $K_2S_2O_7$, $NaHSO_4$.

As a result of using the high purity nickel crucible of the present invention in which the purity of the nickel crucible is 99.9999 wt % or higher, it is possible to perform high purity analysis by inhibiting the mixture of impurities from the crucible. Since the present invention additionally yields a superior effect of saving the labor time and mitigating the amount of reagent to be used, it is possible to meet the demands of recent analytical technology which require fast and accurate measurement of high purity materials.

The invention claimed is:

1. A nickel crucible utilized for melting an analytical sample in the pretreatment of the analytical sample, wherein the purity of the nickel crucible is 99.9999 wt % or higher.

2. A method of treating an analytical sample using a high purity nickel crucible, including a step of preliminarily melting the analytical sample in a nickel crucible having a purity of 99.9999 wt % or higher to obtain the analytical sample.

3. The method of treating an analytical sample according to claim 2, further including steps of weighing and placing the analytical sample in the crucible, and during said preliminary melting step, melting the analytical sample using a basic flux comprising one or more types of alkali chemicals selected from $Na_2CO_3$, $K_2CO_3$, $H_3BO_3$, NaOH, KOH, $Na_2B_2O_7$, and $Li_2B_2O_7$, or said basic flux added with one or more types of oxidizing agents selected from $Na_2O$, $Na_2O_2$, $K_2O$, $K_2O_2$, $KNO_3$, and $KClO_3$, or one or more types of acid flux selected from $Na_2S_2O_7$, $K_2S_2O_7$, and $NaHSO_4$.

4. A method according to claim 2, further comprising the step of analyzing the analytical sample as melted during said preliminary melting step with lower limits of quantification for Mn, Al, Si, Mg, Pb, Fe, Co, Ti, Cu, Cr, Zr, Mo, and W of respectively Mn: 5 wtppm, Al: 10 wtppm, Si: 10 wtppm, Mg: 5 wtppm, Pb: 5 wtppm, Fe: 5 wtppm, Co: 5 wtppm, Ti: 20 wtppm, Cu: 20 wtppm, Cr: 10 wtppm, Zr: 5 wtppm, Mo: 2 wtppm, and W: 10 wtppm.

5. A method of analysis comprising the steps of melting an analytical sample by the use of a nickel crucible having a purity of 99.9999 wt % or higher, and performing analyses with the analytical sample melted during said melting step to obtain analytical results, in which lower limits of quantification for Mn, Al, Si, Mg, Pb, Fe, Co, Ti, Cu, Cr, Zr, Mo, and W are respectively Mn: 5 wtppm, Al: 10 wtppm, Si: 10 wtppm, Mg: 5 wtppm, Pb: 5 wtppm, Fe: 5 wtppm, Co: 5 wtppm, Ti: 20 wtppm, Cu: 20 wtppm, Cr: 10 wtppm, Zr: 5 wtppm, Mo: 2 wtppm, and W: 10 wtppm.

\* \* \* \* \*